United States Patent [19]

Gottlieb et al.

[11] 4,408,085
[45] Oct. 4, 1983

[54] PROCESS FOR PREPARING SEC-BUTYL ALCOHOL AND SEC-BUTYL TERT-BUTYL ETHER

[75] Inventors: Klaus Gottlieb, Herdecke-Ende; Wilfried Graf, Dorsten, both of Fed. Rep. of Germany

[73] Assignee: VEBA OEL AG, Gelsenkirchen-Buer, Fed. Rep. of Germany

[21] Appl. No.: 372,803

[22] Filed: Apr. 28, 1982

[30] Foreign Application Priority Data

Apr. 28, 1981 [DE] Fed. Rep. of Germany ....... 3116780

[51] Int. Cl.³ .................. C07C 41/06; C07C 29/86
[52] U.S. Cl. .................................. 568/697; 568/918
[58] Field of Search ........................... 568/697, 918

[56] References Cited

U.S. PATENT DOCUMENTS

| | | | |
|---|---|---|---|
| 3,119,766 | 1/1964 | Voltz et al. | 568/697 |
| 3,726,942 | 4/1973 | Louder | 568/697 |
| 3,912,463 | 10/1975 | Kozlowski et al. | 568/697 |
| 4,252,541 | 2/1981 | Herbstman | 568/697 |
| 4,329,516 | 5/1982 | Al-Muddarris | 568/697 |

FOREIGN PATENT DOCUMENTS

| | | | |
|---|---|---|---|
| 2040924 | 9/1980 | United Kingdom | 568/697 |
| 2080297 | 2/1982 | United Kingdom | 568/697 |

*Primary Examiner*—J. E. Evans
*Attorney, Agent, or Firm*—Oblon, Fisher, Spivak, McClelland & Maier

[57] ABSTRACT

A process for producing sec-butanol and sec-butyl tert-butyl ether from butane comprises: (a) partially isomerizing n-butane to produce a mixture of n-butane and isobutane; (b) catalytically dehydrogenating said butanes to produce a mixture containing at least butene-1, isobutene and butadiene; (c) selectively hydrogenating butadiene and converting butene-1 to butene-2; (d) etherifying isobutene contained in the dehydrogenation reaction mixture with sec-butanol to form a mixture of sec-butyl tert-butyl ether and unreacted hydrocarbons; (e) converting butene-2 from the unreacted hydrocarbon mixture by hydration to produce sec-butanol; (f) recycling said sec-butanol to the etherification step; recovering said sec-butyl tert-butyl ether.

9 Claims, 1 Drawing Figure

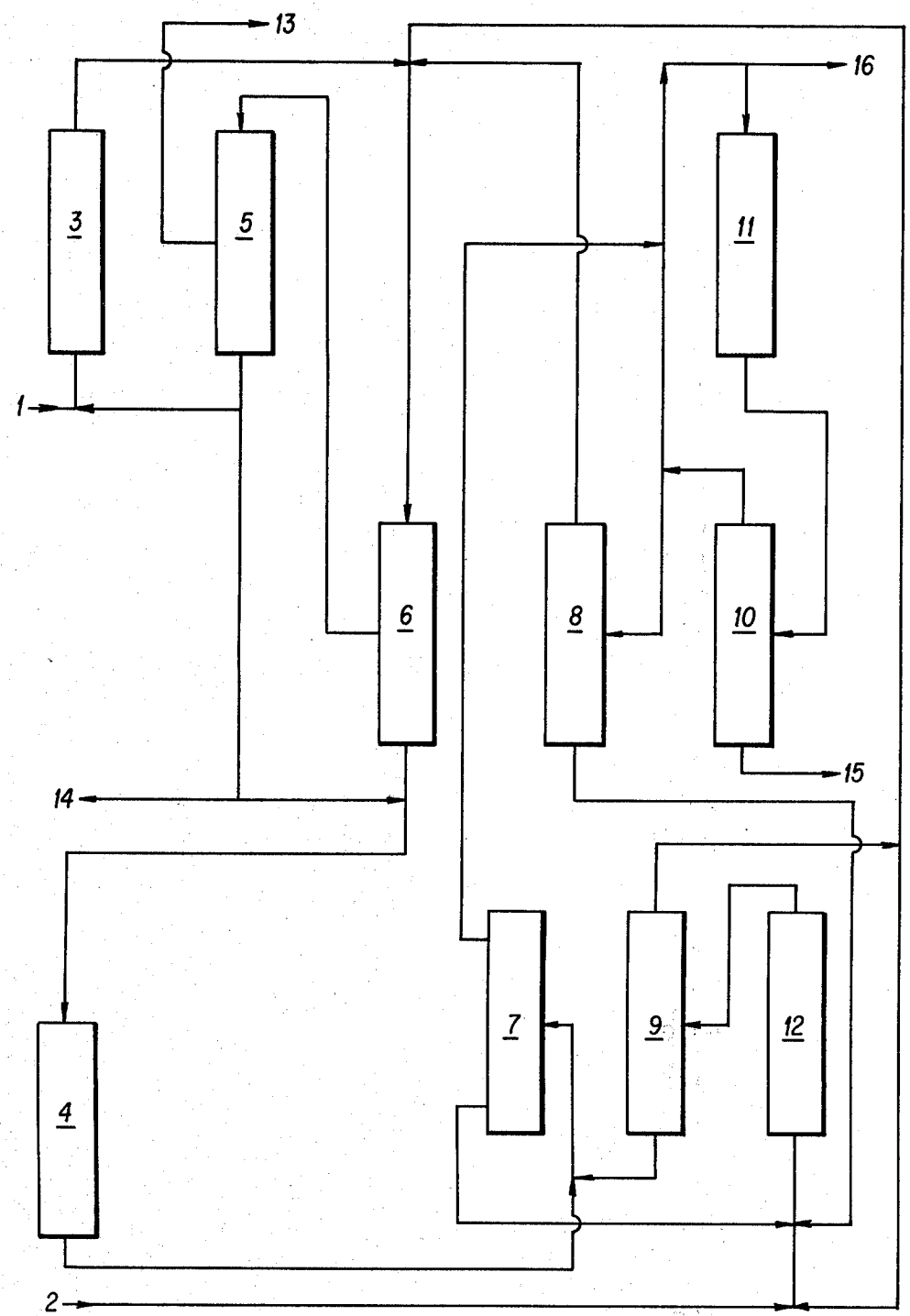

PROCESS FOR PREPARING SEC-BUTYL ALCOHOL AND SEC-BUTYL TERT-BUTYL ETHER

BACKGROUND OF THE INVENTION

1. Field of the Invention

This invention relates to a process for producing sec-butanol and sec-butyl tert-butyl ether and possibly tert-butyl alcohol from hydrocarbon mixtures containing butane, such as occur in crude oil production or crude oil refining.

2. Description of the Prior Art

It is known from German OS No. 26 20 011 and OS 29 21 576 to convert butane into methyl tert-butyl ether. In those processes n-butane is partially or completely isomerized into isobutane (2-methylpropane) and the n-butane-isobutane mixture is dehydrogenated forming n-butenes in addition to isobutene. The dehydrogenation reaction mixture is then etherified with an excess of methanol, whereby the isobutene formed in the dehydrogenation step is converted to methyl tert-butyl ether. The excess methanol from the etherification reaction mixture can be removed either with water or by azeotropic distillation.

SUMMARY OF THE INVENTION

According to the present invention, however, n-butenes arising from the dehydrogenation of n-butane are converted into sec-butyl alcohol and into the sec-butyl tert-butyl ether prepared from it.

In this regard, according to the present invention, n-butane is partially isomerized, catalytically dehydrogenated, butadiene in the dehydrogenation reaction mixture is selectively hydrogenated, with simultaneous conversion of butene-1 into butene-2, and the isobutene contained in the dehydrogenation mixture after selective hydrogenation is reacted with recycled sec-butyl alcohol to form sec-butyl tert-butyl ether. The sec-butyl alcohol is prepared by reaction of water with the butene-2 of the hydrocarbon mixture, which contains principally butene-2 and butene, after the etherification. The invention also assures production of the tert-butyl alcohol (2-methylpropan-2-ol) in particular mixed with sec-butyl alcohol and sec-butyl tert-butyl ether from sec-butyl alcohol which contains water and isobutene.

BRIEF DESCRIPTION OF THE DRAWINGS

Further features of the invention will be apparent from the following description of the process in which the process is explained in more detail with reference to the flow chart in the accompanying drawing. The drawing illustrates a preferred embodiment of the process of the invention. Parts which are not necessary for an understanding of the principle, such as pumps, heat exchangers, some distillation columns and the like, are omitted.

DESCRIPTION OF THE PREFERRED EMBODIMENTS n-Butane, which may contain isobutane, e.g., a butane fraction of the gases occurring in the production or refining of petroleum, is fed to an isomerization reactor 3. The isomerization, n-butane to isobutane, takes place in a conventional manner on a platinum-containing fixed bed catalyst in the presence of hydrogen at temperatures of 150°–210° C., and preferably at pressures of 15–30 bar. The reaction conditions of pressure and temperature are so controlled that the isomerization equilibrium is reached to the greatest extent possible. The hydrogen and the methane, ethane and propane formed in the isomerization are separated from the reaction mixture leaving the isomerization reactor 3, which comprises up to 50% by weight of isobutane. The isomerizate is taken to dehydrogenation 6 together with the recycled isobutane from etherification and the recycled hydrocarbons from the hydration.

Isomerization converts enough of the n-butane into isobutane as is needed for use as the predetermined stoichiometric amount for the etherification of the total amount of alcohol produced. The isobutane content of the butane stream after isomerization is 40–55% by weight.

Dehydrogenation 6 of the $C_4$-hydrocarbons takes place catalytically by conventional procedures either in a fixed bed or a fluidized bed reactor. The dehydrogenation temperature is between 530° and 700° C., the pressure between 0.2 and 5 bar, preferably about 0.3 and 1.5 bar. The dehydrogenation catalyst consists generally of active aluminum oxide with additives of chromium oxide or platinum, which are applied to the $Al_2O_3$ by impregnation. The coke produced during the reaction phase is burned off with air in a regeneration phase; the heat released in this process is recovered and used as process heat. The dehydrogenation reaction mixture is separated by cooling and compression into a gaseous stream containing predominantly light hydrocarbons and the hydrogen and a liquid stream containing the butane, butadiene and butenes.

The hydrogen is removed to a large extent from the gaseous stream in a purifying unit 5 by conventional procedures. If there is no adequate use for the total amount of hydrogen, only so much of the hydrogen is removed from the light fraction of the dehydrogenation mixture as is needed for the isomerization and hydrogenation reactions. The remaining hydrogen can be removed at 14 and the dehydrogenation waste gas can be removed at 13 to produce process energy. The stream containing all hydrocarbons is taken to selective hydrogenation and hydroisomerization 4, wherein butadiene is selectively hydrogenated to butene and at the same time all butene-1 is converted into butene-2.

Selective hydrogenation and hydroisomerization are carried out by conventional procedures, i.e. catalytically in the presence of hydrogen in a fixed bed reactor. The temperature is 20°–80° C., preferably 30°–60° C., the pressure 1–20 bar, preferably 1.5–10 bar. The catalyst consists in general of a carrier, e.g. aluminum oxide or silicon oxide and additives of platinum, palladium or nickel.

The hydrogen concentration and the feed rate are selected so that the conversion of butadiene is almost complete (a residual content of butadiene in the final reaction mixture less than 0.5% by weight) and the yield of butene-1 converted into butene-2 is at a maximum near the thermodynamic equilibrium value, and so that the butenes are hydrogenated in as small amount as possible (less than 10% by weight) to n-butane.

The purpose of this step is to allow isobutane to be separated by distillation after etherification so that butenes and n-butane remain in the sump of the column 8. The boiling point difference between isobutane on the one hand, and n-butane and butene-2 on the other is so great that a simple distillative separation of isobutane is possible if butene-1 is previously converted by hydroisomerization into butene-2 and isobutene is separated by etherification. In a particular embodiment of the method according to the invention selective hydrogenation and hydroisomerization are carried out after etherification; this is preferable if the polymeric materials, which are under these circumstances, formed in small amounts from butadiene, cause no noticeable inconvenience in the etherification, by reason of the process conditions chosen for the etherification.

Isobutene and sec-butanol are catalytically etherified, whereby from 10 to 100%, preferably from 50 to 90%, of the sec-butyl alcohol is reacted to form sec-butyl tert-butyl ether. Tert-butanol and trimethylpentenes are formed in small amounts. It has been found that n-butenes undergo no reaction and leave the reactor unchanged. Sulfonated cation exchanger resins serve as catalysts, the most preferred being strongly acid ion exchangers based on sulfonated styrene cross-linked with divinylbenzene. Etherification takes places in the liquid phase in a single or multi-staged fixed bed reactor 11 at temperatures between 20° and 150° C., preferably at 30° to 60° C. and pressures of 4 to 40 bar, preferably 8 to 16 bar. The molar ratio of sec-butanol to isobutene should be in the range of 1:0.5 to 1:10, preferably 1:1 to 1:3; the space velocity, expressed in liters of feed per liter of catalyst per hour should be in the range of 0.3 to 50, preferably 1 to 20.

The stream leaving the etherification reactor 11 consists primarily of sec-butyl tert-butyl ether, unconverted isobutene, sec-butyl alcohol and possibly butene and butane. The mixture is taken to a pressure distillation column 10 in order to separate the sec-butyl tert-butyl ether. The unconverted $C_4$-hydrocarbons containing unconverted isobutene are withdrawn overhead and recycled in the etherification 11 in order to obtain a high total conversion of isobutene. The ether-alcohol mixture withdrawn from the bottom of column 10 can be separated into an ether-alcohol-azeotrope and pure ether; the ether is then drawn off from the bottom of the azeotrope distillation unit, the ether-alcohol mixture is withdrawn overhead and recycled to the etherification.

The ether-alcohol mixture from the bottom of column 10 can also be separated by washing with water into a water-alcohol phase and an ether phase. In this process one part of ether-alcohol mixture is added to twenty parts of water, preferably 5 to 10 parts of water, and this total mixture is thoroughly mixed at 15°–20° C., preferably 20°–40° C. Separation into an ether phase and a water-alcohol phase can be carried out, for example, according to the mixer-settler principle. The separated ether raffinate contains 0.5–5% by weight of trimethylpentenes and less than 2% by weight of sec-butyl alcohol, 1% by weight of isobutene, 0.5% by weight of tert-butyl alcohol and 0.2% by weight of water.

The water needed for the water wash consists in part of the recycled water from the hydration 12 and the remainder of the fresh water 2 needed for hydration. The water phase containing sec-butyl alcohol removed from the water wash can be recycled to the hydration 12 and processed together with the reaction mixture from the hydration reactor.

If, in accordance with the preferred embodiment, an ether-sec-butyl alcohol mixture is to be produced, then sec-butyl alcohol is etherified with such an excess of isobutene that a separation of unconverted sec-butanol is not necessary. In that case an ether-alcohol mixture is drawn off from the bottom of the pressure column at 15.

The production of sec-butyl tert-butyl ether is known from German OS No. 25 35 471 and OS No. 26 20 011. In contrast to the embodiments described there, which are based on an excess of sec-butyl alcohol during the reaction and higher temperatures, the present procedure uses an excess of isobutene and low temperatures in order to achieve the highest possible conversion of sec-butyl alcohol and thus to eliminate any separation and recycling of unconverted sec-butyl alcohol. Also, for the embodiment described above in which the unconverted sec-butyl alcohol is separated by treatment with water, it is more economical to operate with an excess of isobutene and the highest possible sec-butyl alcohol conversion.

In a particular embodiment of the method according to the invention the $C_4$-fraction containing isobutene is reacted with a mixture of sec-butyl alcohol and water in the presence of acid catalysts, whereby between 10–95, preferably 50–90%, of the sec-butyl alcohol is converted to form 50–100% sec-butyl tert-butyl ether and 50–100% of the water is reacted to form tert-butyl alcohol. The sec-butyl alcohol-water mixture used as feed can contain 1–50% by weight of water; in particular, a sec-butyl alcohol-water mixture produced in an azeotropic distillation can be used. It has been found that even in the presence of water the n-butenes undergo no reaction. Surprisingly it has also been found that tert-butyl alcohol forms no reaction product through parallel reaction with isobutene. The same sulfonated, strongly acidic ion exchangers can serve as catalysts in the embodiment described above. The reaction takes place in a multi-staged fixed bed reactor at temperatures between 20°–150° C., preferably 30°–80° C. and pressures from 4–40 bar, preferably 8–16 bar. The molar ratio of sec-butyl alcohol to isobutene is in the range of 1:0.1 to 1:10, preferably 1:0.7 to 1:5; the molar ratio of water to isobutene is in the range of 1:1 to 1:20, preferably 1:1.5 to 1:10; the space velocity in liters of feed per liter of catalyst per hour is in the range of 0.3 to 50, preferably 1 to 20. The ether-alcohol mixture is separated by distillation under pressure from the unconverted hydrocarbons which are then recycled, as was described in relation to the above embodiment wherein sec-butyl alcohol is etherified without the addition of water.

The $C_4$-fraction separated after etherification, containing only isobutane, n-butane and n-butene, is taken to a pressure distillation column 8 where isobutane is separated from the other $C_4$-hydrocarbons. Isobutane is recycled to the dehydrogenation 6, the butene fraction drawn off from the bottom is taken to the butene hydration 12, where sec-butyl alcohol is produced by catalytic synthesis from butene and water at a pressure of 20–80 bar and 100°–170° C., preferably 30–60 bar and 120°–160° C. Strongly acidic ion exchangers are used as catalysts; the most preferred are sulfonated polystyrene resins cross-linked with divinyl benzene. In the feed stream 2–10 moles, preferably 3–6 moles, of water are used per one mole of butene. The space velocity in liters of feed per liter of catalyst per hour is 0.2–15, preferably 0.5–5. Under these reaction conditions 5–35% of the n-butene that is used is converted to form sec-butyl alcohol and traces of di-sec-butyl ether. The $C_4$-hydrocarbons are removed from the reaction mixture as overhead from the column 9 in a simple distillation, and a partial stream is recycled to the hydration reactor 12. A quantitatively smaller partial stream is recycled to the dehydrogenation 6. The sec-butyl alcohol-water mixture, which may be combined with the sec-butyl alcohol-water mixture used in the water wash of the etherification 11, may be mixed, after distillative enrichment of sec-butyl alcohol, with a water insoluble organic solvent which separates easily from sec-butyl alcohol and is suitable as an extraction medium for sec-butyl alcohol. According to a particular embodiment of this invention one of the C$_4$-streams containing n-butene or isobutene produced in the procedure is used for that. After separating the extraction mixture into an organic phase and an aqueous phase, the organic phase contains 50–98% of the sec-butyl alcohol that is produced and 90–98% of the di-sec-butyl ether. The C$_4$-hydrocarbons are separated from the organic phase by distillation and recycled to the extraction step 7. The sec-butyl alcohol removed from the distillation sump is taken to the etherification along with the di-sec-butyl ether that is formed.

In the preferred embodiment the C$_4$-fraction containing isobutene is used for extraction 7. One part by weight of the water-sec-butyl alcohol mixture withdrawn from the bottom of the column 9 is mixed with 2–10 parts by weight of the C$_4$-fraction and is taken to the extraction step 7, where the total mixture is separated into an aqueous and an organic phase. The organic phase contains 50–80% by weight of the sec-butyl alcohol fed to the extraction and small amounts of water. A mixture, containing a small amount of water, of sec-butyl alcohol and a C$_4$-fraction containing isobutene is separated by distillation. This mixture contains isobutene and sec-butyl alcohol in the necessary stoichiometric amounts for the etherification 11. If, in addition to sec-butyl tert-butyl ether, sec-butyl alcohol is also to be produced, then the organic phase is completely separated by distillation into sec-butyl alcohol and the C$_4$-fraction containing isobutene, and sec-butyl alcohol is withdrawn from the sump of the rectifier column at 16. The etherification to produce sec-butyl tert-butyl ether is fed, in this case, with separate streams of sec-butyl alcohol and the C$_4$-fraction containing isobutene. The aqueous phase separated in extraction, which is depleted of sec-butyl alcohol, is recycled to the hydration 12.

In order to increase the separation capacity of the extraction step, a sec-butyl alcohol-water mixture enriched in sec-butyl alcohol can first be separated by distillation from the sec-butyl alcohol-water mixture withdrawn from the bottom of the column 9, and, as was described above, treated with the C$_4$-fraction containing isobutene. The degree of enrichment can be up to 80% by weight. To separate sec-butyl alcohol by extraction, one part by weight of the aqueous mixture enriched in sec-butyl alcohol in mixed with 0.5–5 parts by weight of C$_4$-fraction containing isobutene. This is then taken to the extraction step 7, where 80–98% by weight of the sec-butyl alcohol in the organic phase which was formed in the hydration is separated. Water is recycled again to the hydration. Instead of the C$_4$-fraction containing isobutene, the isobutene-free C$_4$-fraction containing butene-2 and n-butane from the input to the butene hydration 12 can also be used as the extraction medium.

Finally, in a special embodiment of the process according to the invention a sec-butyl alcohol-water mixture that is withdrawn after hydration 12 from the top of an enrichment column can be directly fed to the etherification 11, and the ether-alcohol mixture containing tert-butyl alcohol according to the invention can be produced and drawn off at 15.

Having now generally described the invention, a further understanding may be obtained by reference to the following illustrating examples, which are included herein for the purposes of illustration only and are not intended to be limiting unless so specified.

EXAMPLE 1

Isobutene and sec-butyl alcohol were mixed in a molar ratio of 1.4:1 at a temperature of 40° C. and a pressure above the vapor pressure of isobutene, namely 16 bar, so that they formed a liquid. A slender tube reactor with a ratio of interior diameter to length of 1:30 was used as the reactor and a strongly acidic ion exchange resin (commercial product Amberlyst 15) was used as a catalyst. The reactor, filled with catalyst, was fed with 11.8 parts by weight of said sec-butyl alcoholisobutene mixture per hour per part by weight of dry catalyst. A suitable pre-heater was used to establish the designated temperature; the heat liberated during the reaction was removed through a cooler. The reaction mixture was largely freed by distillation of the unconverted isobutene and had the composition given in the table, Example 1a. The sec-butyl alcohol conversion was 78.1%, the yield of sec-butyl tert-butyl ether was 77.6 mole-%, based on the amount of sec-butyl alcohol used. The stabilized phase with the composition set out above was washed twice, in each case with three volumes of water and largely freed of sec-butyl alcohol. The ether phase produced after this water wash had the composition shown in the Table, Example 1b.

EXAMPLE 2

Isobutene and sec-butyl alcohol were reacted in a molar ratio of 1.8:1 at a temperature of 30° C. on a strongly acidic ion exchanger resin (commercial product Amberlyst 15). The reactor, filled with catalyst, was fed with 6.9 parts by weight of the specified sec-butyl alcohol-isobutene mixture. The other conditions corresponded to those in Example 1. The reaction mixture was largely freed of unconverted isobutene by distillation and had the composition shown in the table.

EXAMPLE 3

A mixture containing 0.46 moles of water and 0.64 moles of sec-butyl alcohol was reacted with isobutene in a molar ratio of water:sec-butyl alcohol:isobutene=0.46:0.64:0.96 at a temperature of 60° C. The reactor, filled with a catalyst, was fed with 4.4 parts by weight of the specified mixture of water, sec-butyl alcohol and isobutene per hour per part by weight of dry catalyst. The other conditions corresponded to those given in Example 1. The organic phase of the final reaction mixture was largely freed of unconverted isobutene by distillation and had the composition given in the table.

TABLE

| Components/Example | 1a | 1b | 2 | 3 |
|---|---|---|---|---|
| i-butene | 0.8 | 0.9 | 0.7 | 0.7 |
| tert-butyl alcohol | 0.4 | 0.4 | 0.4 | 27.2 |
| sec-butyl alcohol | 12.5 | 1.8 | 3.8 | 33.0 |
| trimethylpentenes | 3.4 | 3.8 | 4.6 | 1.8 |
| sec-butyl tert-butyl ether | 82.8 | 92.7 | 90.3 | 37.0 |
| H$_2$O | <0.1 | 0.2 | <0.1 | 0.3 |

It is understood that various changes and modifications in light hereof will be apparent to those skilled in the art and are within the purview of this invention.

What is claimed as new and desired to be secured by Letters Patent of the United States is:

1. A process for producing sec-butanol and sec-butyl tert-butyl ether from butane comprising:
    (a) partially isomerizing n-butane to produce a mixture of n-butane and isobutane;
    (b) catalytically dehydrogenating the mixture of n-butane and iso-butane from step (a) to produce a mixture containing at least butene-1, iso-butene and butadiene;
    (c) selectively hydrogenating and hydroisomerizing the mixture from step (b) so as to convert at least a part of the butadiene to butene-1 and to convert essentially all of the butene-1, that from the dehydrogenation step (b) and from the selective hydrogenation of butadiene, to butene-2, whereby a mixture of $C_4$-hydrocarbons is produced which contains at least unreacted isobutene from step (b) and butene-2;
    (d) etherifying at least a part of the isobutene contained in the mixture obtained from step (c) with sec-butanol to form a mixture containing at least sec-butyl tert-butyl ether and unreacted hydrocarbons, including butene-2;
    (e) converting at least a part of the butene-2 contained in the unreacted hydrocarbons of step (d) to sec-butanol by a hydration reaction;
    (f) recycling the sec-butanol of step (e) to the etherification step (d);
    (g) recovering the sec-butyl tert butyl ether reaction product of step (d).

2. The process according to claim 1, wherein any unreacted isobutene from etherification step (d) and the unconverted hydrocarbons from the hydration reaction step (e) are recycled to the catalytic dehydrogenation step (b).

3. The process according to claim 1 or 2, wherein said etherification of step (d) is conducted in the presence of acid catalysts at temperatures of 20°–150° C., using 0.5–10 moles preferably 1–3 moles of isobutene per 1 mole of sec-butanol.

4. The process according to claim 1 or 2 wherein unconverted sec-butanol is extracted from the etherification reaction product mixture of step (d) by treating said mixture with water.

5. The process according to claim 1 or 2, wherein a mixture of sec-butanol and water is reacted with said product mixture from step (c) at temperatures of 20°–150° C. in the presence of acid catalysts to form tert-butanol and sec-butyl tert-butyl ether and wherein the amount of isobutene present is sufficient to provide 0.1–10 moles of isobutene per 1 mole of sec-butanol and 1–20 moles of isobutene per 1 mole of water.

6. The process according to claim 1 or 2 wherein a water-sec-butanol mixture is separated from the hydration reaction product of step (e) by rectification, sec-butanol is then extractively separated from said water-sec-butanol mixture by treatment with said mixture of $C_4$-hydrocarbons containing isobutene of step (c), whereby an organic phase containing at least sec-butanol and said $C_4$-hydrocarbons containing isobutene, and an aqueous phase, are formed, said organic phase is separated by distillation, whereby a mixture of sec-butanol and isobutene is separated from the other $C_4$ hydrocarbons and said mixture is then sent to etherification step (d), said $C_4$-hydrocarbons, separated from the sec-butanol by distillation, are recycled to said extraction step, and the aqueous phase from said extraction step is recycled back to the hydration step (e).

7. The process according to claims 1 or 2 wherein sec-butanol is extracted from the hydration reaction product mixture of step (e) by treatment of said reaction product mixture with a hydrocarbon mixture consisting predominantly of n-butane and butene-2 whereby an organic phase containing sec-butanol, n-butane and butene-2 is formed and also an aqueous phase is formed, said organic phase is separated by distillation into a sec-butanol fraction and a hydrocabon fraction, said sec-butanol is taken to etherification step (d) while the hydrocarbon fraction freed from sec-butanol is proportionately recycled to the hydration step (e) and the extraction step and, the aqueous phase from the extraction step is recycled to the hydration step (e).

8. The process according to claim 1 or 2 wherein the sec-butyl tert-butyl ether reaction product of step (d) is recovered in substantially pure form by a pressure distillation step to recover a mixture of said ether and sec-butyl alcohol, followed by washing with water to provide an ether phase and an alcohol-water phase and finally, separating the two phases.

9. The process according to claim 1 or 2 wherein the sec-butyl tert-butyl ether is recovered as a mixture of sec-butyl alcohol and said ether by adjusting the proportions of sec-butyl alcohol and isobutene in step (d) so as to provide a final product containing the desired ratio of said ether and said alcohol and separating said mixture of alcohol and ether from said unreacted hydrocarbons.

* * * * *